United States Patent [19]

Duret et al.

[11] Patent Number: 4,611,288

[45] Date of Patent: Sep. 9, 1986

[54] APPARATUS FOR TAKING ODONTOLOGICAL OR MEDICAL IMPRESSIONS

[76] Inventors: François Duret; Elisabeth Duret nee Michallet, both of rue Paul Claudel, Le Grand Lemps; Christian Thermoz, 2, place Victor Hugo, Grenoble, all of France

[21] Appl. No.: 485,059

[22] Filed: Apr. 14, 1983

[30] Foreign Application Priority Data

Apr. 14, 1982 [FR] France ................ 82 06707

[51] Int. Cl.[4] .............. G06F 15/46; G06F 15/42; A61C 13/00
[52] U.S. Cl. .................. 364/474; 364/167; 364/413; 433/25; 433/213; 128/665
[58] Field of Search ................. 364/167–168, 364/413–415, 417, 474–475; 433/25, 54, 212–214; 128/653, 665, 362

[56] References Cited

U.S. PATENT DOCUMENTS

| | | | |
|---|---|---|---|
| 4,072,289 | 2/1978 | Brueckner et al. | 364/414 X |
| 4,074,564 | 2/1978 | Anderson | 364/414 X |
| 4,075,883 | 2/1978 | Glover | 364/414 X |
| 4,136,388 | 1/1979 | Lindquist | 364/414 |
| 4,182,316 | 1/1980 | Nilsson et al. | 128/665 |
| 4,197,885 | 4/1980 | Lewin | 128/653 |
| 4,290,433 | 9/1981 | Alfano | 128/665 |
| 4,324,546 | 4/1982 | Heitlinger et al. | 433/25 |

Primary Examiner—Gary V. Harkcom
Attorney, Agent, or Firm—Karl F. Ross; Herbert Dubno

[57] ABSTRACT

Dental prostheses, such as crowns, inlays or dentures are produced automatically based upon an optical impression taken of the oral region wtih nontraumatic radiation. The reflected waves are transformed into numerical data which is used directly to operate a numerically controlled machine in the fabrication process. The process is pertinent to other medical applications as well.

5 Claims, 37 Drawing Figures

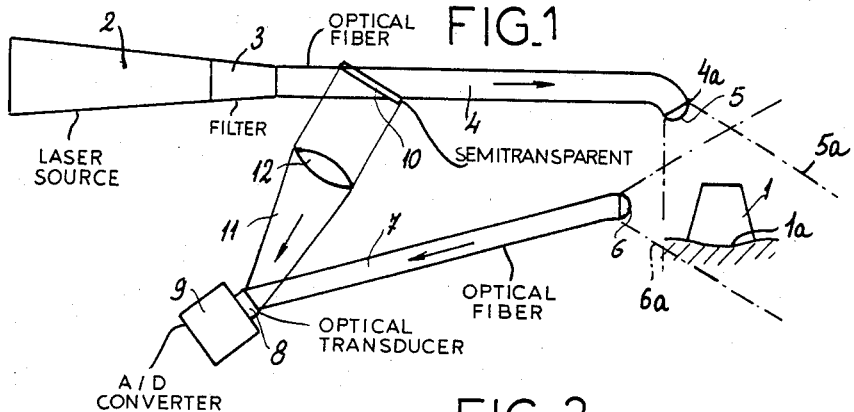
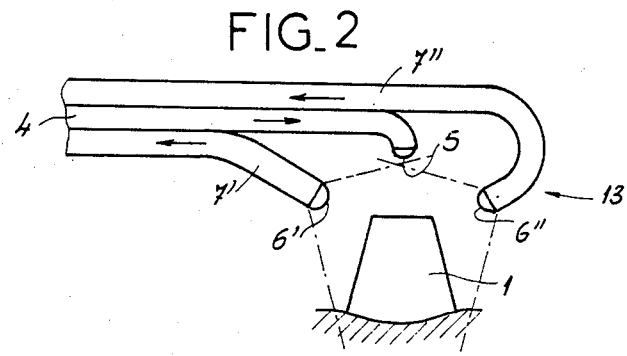
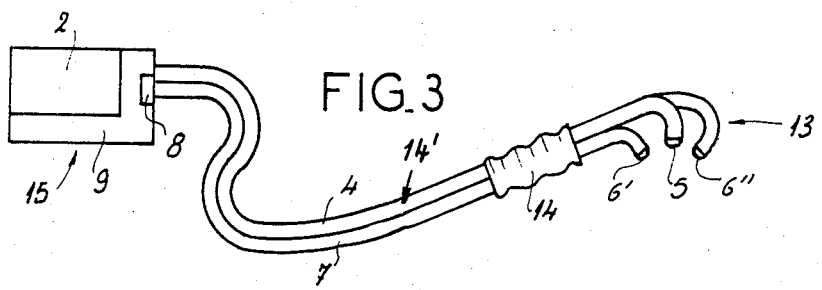
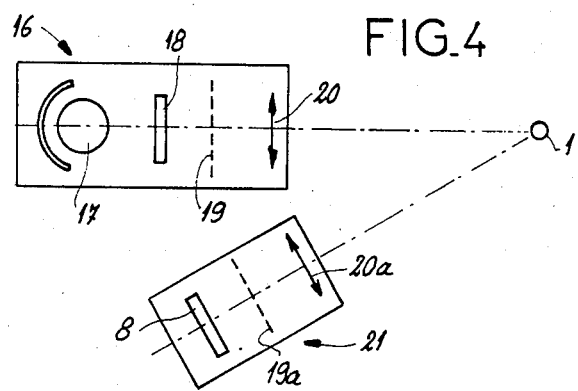

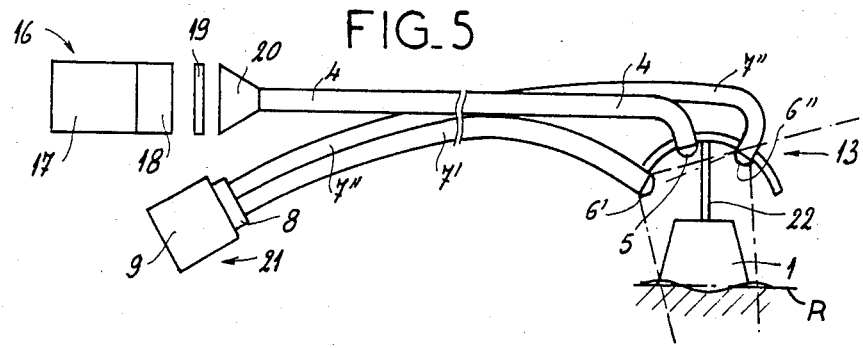
FIG_5
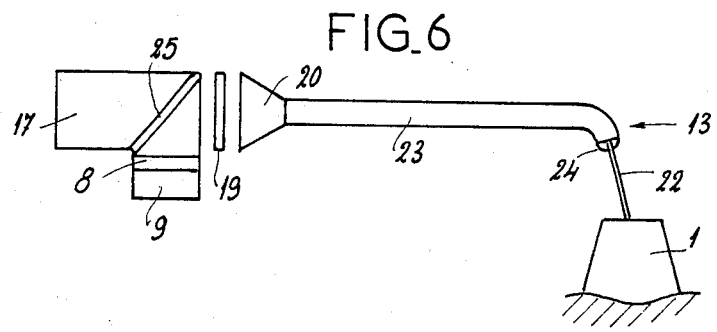
FIG_6
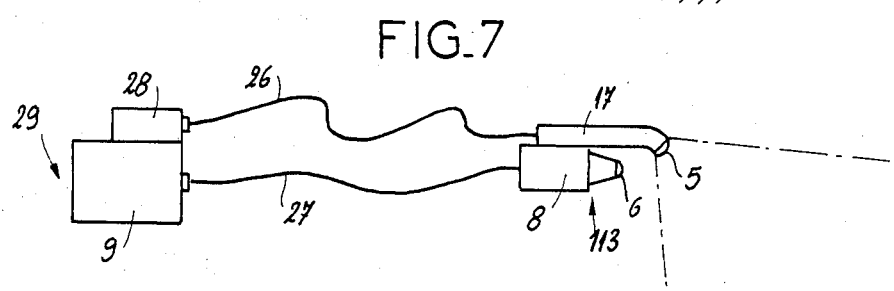
FIG_7
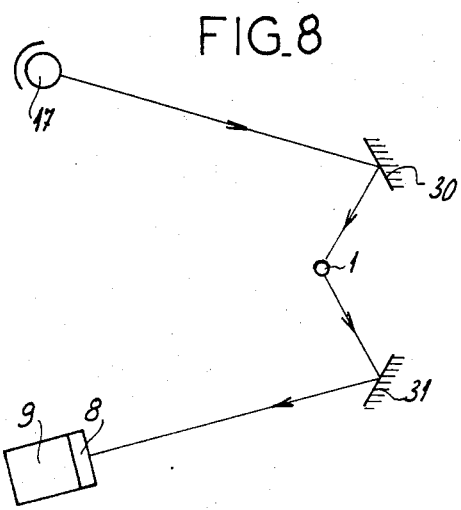
FIG_8

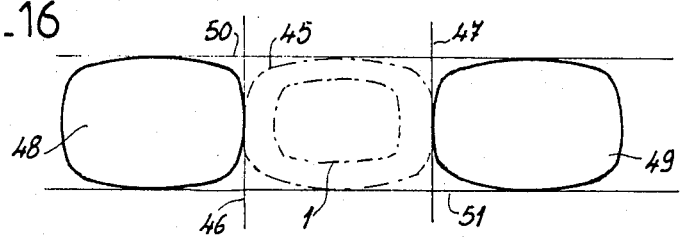
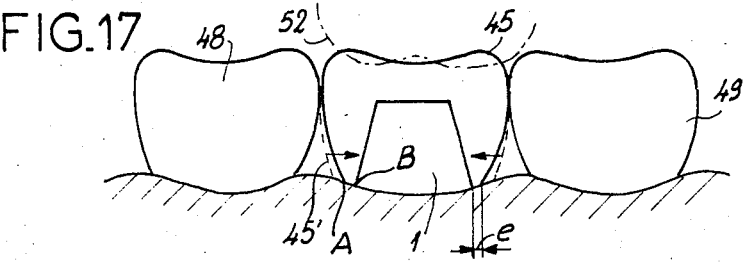
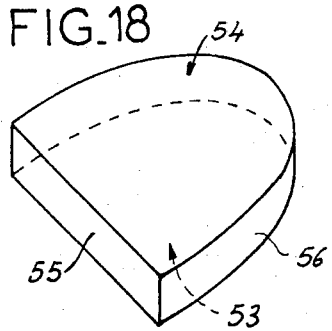
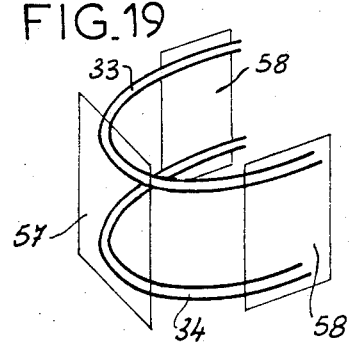
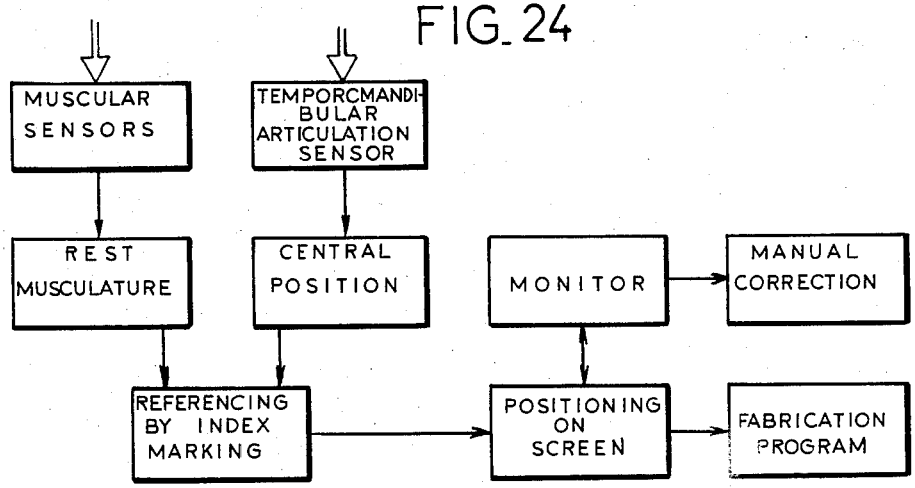

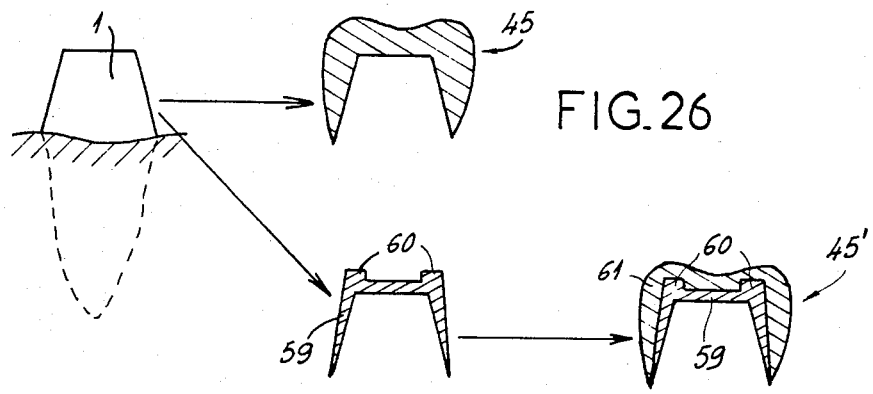
FIG. 26
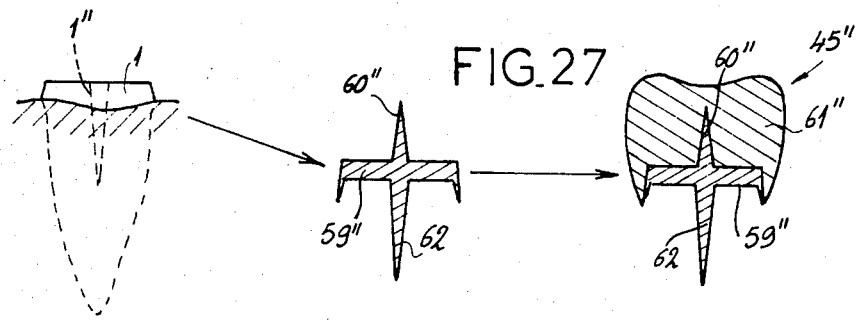
FIG. 27
FIG. 28  FIG. 29  FIG. 30
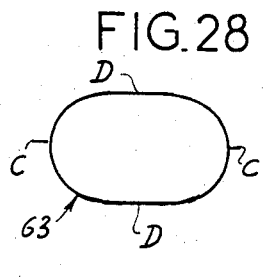 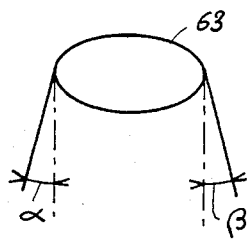 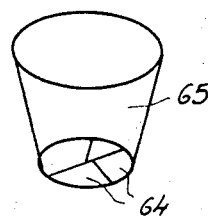

APPARATUS FOR TAKING ODONTOLOGICAL OR MEDICAL IMPRESSIONS

CROSS REFERENCE TO RELATED APPLICATION

This application is related to the commonly owned application Ser. No. 262,905 filed May 12, 1981 (now abandoned) and which is hereby incorporated by reference to the extent necessary for clarification of the concepts here involved with respect to the fabrication of crowns. Ser. No. 262,905 has been replaced by a continuation Ser. No. 580,776 filed Feb. 21, 1984, now also abandoned and replaced by copending continuation-in-part application Ser. No. 673,655 filed Nov. 21, 1984. Reference may also be had to the art cited in the file of this application and which applicants believe, apart from the reference discussed more fully below, to be the best art available dealing with this subject matter or analogous or related subject matters. To the extent necessary, moreover, reference may be had to the French application No. 82 06 707 of Apr. 14, 1982 upon which the present application is based.

FIELD OF THE INVENTION

Our present invention relates to an apparatus for forming a three dimensional structure, primarily for dental and medical applications and, more particularly, to a method of and to an apparatus for taking odontological and medical impressions using radiant energy and specifically for the automatic or semiautomatic substantial production of a prosthesis.

The invention is especially applicable in dentistry for the production of prosthetic devices such as crowns, although unless indicated otherwise, it should not be considered to be limited to the dentistry field or to this specific application in the dental field since it is also applicable, for example, to the design and fabrication of prosthetic devices for bone fitting purposes and even to the taking of an impression or generating a model in dental applications which are not followed by fabrication of a prosthesis.

BACKGROUND OF THE INVENTION

While considerable effort is continuously being expended in the improvement of dental prostheses, until now there has been no commercially satisfactory approach utilizing optical means for the taking of an impression for the purposes of fabricating such a prosthesis. The term "taking an impression" is here used to refer to the generation of an intangible model based upon which a prosthesis can be fabricated, whether or not this modelling, generally is followed by the actual fabrication of a prosthesis.

This is not to say that efforts have not been made to develop optical means for making such models or taking such impressions.

In U.S. Pat. No. 3,861,044, for example, a method has been described for taking an impression of a cavity or fitting a prosthetic device in the form of an inlay into the cavity, which comprises:

preparing the defective tooth;

producing a photographic representation of the tooth with the cavity intended to receive the inlay;

generating a signal representing the photographic image and using it to control an automatic machine tool;

filling the cavity with wax;

producing a second photographic representation of the tooth with the cavity filled with the wax;

generating another signal for the machine tool based upon the second photographic representation;

operating the machine tool to produce the inlay or insert; and placing the machined inlay or insert in the cavity.

This approach, while demonstrating that the use of optical means has been recognized as a possibility in the odontology, has a number of drawbacks which, among others may have been the reason why it has not found commercial success.

Firstly, an ordinary photographic image is capable only of providing a two dimensional representation of the object whose shape is to be analyzed. If one wishes a three dimensional representation utilizing a photographic approach of this type, it is necessary to generate a large number of photographs, say a thousand or more, reproducing successive planes in the third dimension, the photographs representing, in turn, sections which must be accurately positioned with a precision of 100 microns or less for practical purposes.

Secondly, from the reference, it is not clear how the machine tool can actually be controlled from the photographic representations and, specifically, whether analog or digital signals are utilized, and how, for example, a numerically controlled machine tool may be operated from the photographs. Experience with the use of photographic representations has shown that they do not provide the precision, accurate positioning and resolution required for effective translation into control signals, especially for numerically controlled machine tools.

Thirdly, with the system described in that patent, the practitioner must fill the cavity with wax, a technique which may have meaning for the preparation of inlays, but which of course is meaningless when, for example, prosthetic crowns are to be prepared. Thus the method of that patent had only limited applicability, i.e. was not sufficiently versatile for widespread or even commercial use.

Finally, because the actual impression involves the introduction of a moldable material, namely wax, into the cavity, the mouth is not strictly an optical or radiation approach to the taking of the impression or the fitting. Since a second photograph is required and there is a time between the photographs, conditions may change, a factor leading to a reduction in precision. Furthermore, the difficulty of translating the two photographic representations into a three dimensional representation also creates problems with respect to precision.

OBJECTS OF THE INVENTION

It is, therefore, the principal object of the present invention to provide an improved apparatus for taking medical or dental impressions which provides a three dimensional modeling adaptable practically to all odontological and medical applications, with high precision and for direct control of a machine tool for fabricating a prosthesis.

Another object of the invention is to provide a method of and an apparatus for producing dental prostheses, including crowns, with a high degree of precision at comparatively low cost and with practically total automation starting from taking the impression and running through the generation of the completed prosthesis so that intermediate models, a plurality of fittings and like noisome operations are eliminated.

It is another object of this invention to provide an apparatus for the purposes described which have great versatility, are easily manipulated and utilized even by one with minimal skills and can reduce the length of time required to produce a prosthetic device and the cost of fabricating it.

SUMMARY OF THE INVENTION

These objects and others which will become apparent hereinafter are attained, in accordance with the present invention, in a device and method for automatically producing a prosthesis and for taking an impression by optical means, especially for the fabrication and fitting of the prosthesis with high precision which comprises at least one light emitter, means for directing this radiation against a portion of the body, for example the region of a tooth upon which a prosthetic device is to be fitted, receiving means responsive to the luminous or acoustic radiation reflected from this part of the body, transducer means responsive to the reflected radiation for translating same into a signal and including analog-numerical or analog-digital converter, so that the signal is in numerical terms and represents the space of the body part undergoing analysis in three dimensions. Means is provided to analyze and process the numerical signals obtained for automatically operating a numerically controlled N-C machine easily with this signal to produce a prosthesis adapted to fit perfectly on this body part.

The apparatus of the invention allows all of the characteristics of the zone to be analyzed to be determined solely by radiant energy means, without any intervening graphic display i.e. by an optic means which can eliminate the photographic representations hitherto considered to be necessary.

The term "optic" is here used to refer to radiant energy of a form usually described as optical, namely, light. Naturally, the effective radiant energy must be such that it can give by reflection the three dimensional representation of the region from which the radiant energy is reflected and must also be such that it is not traumatic for the tissues of the part of the body subjected to this analysis or the surrounding tissues of the patient. The receiver and the converter or transducer which is utilized in accordance with the invention will of course correspond to the type of radiant energy utilized and should be such that it is capable of providing an output representing the three dimensional image with a precision greater than or equal to a millimeter.

According to a feature of the invention, the radiant energy which in used in coherent light and, preferably the emitter comprises a laser source, at least one fiber optic light path connected to this source and a lens in this light path for directing a pencil of laser illumination toward the part of the body to be analyzed. At least one other lens, forming a collecting lens and another optical fiber light pipe is used to receive the reflected rays for conducting the collected light to a receiver associated with an analog-numerical converter. Advantageously, an optical system utilizing a semitransparent mirror and a lens can direct a portion of the light from the emitter to the receiver to provide a reference input to the latter so that by interference analysis between the reference beam and the reflected rays, the shape of the object from which the reflected rays arise can be analyzed.

The laser source, the receiver and the converter can thus be disposed in a housing outside the mouth and connected to the site at which the laser beam is directed onto the portion of the body to be analyzed and from which the reflected rays arise, by light pipes terminating in an analysis head which can be of small dimensions and which can be introduced into the mouth of the patient.

Alternatively a single optical fiber light pipe can be utilized to supply the incident light rays and to guiding the reflected light rays to the housing. Naturally, where the light source and the receiver are of small dimensions, the light pipes and optical fiber paths can be eliminated entirely since the emitter and receiver can be provided directly in the analysis head. The head then will have the lenses necessary for directing the beam and for collecting the rays and will be connected by electric lines to the converter and other electrical circuitry which can be located outside the mouth.

One method which we may use and which avoids the need for analysis or reading of a hologram utilizes a laser emitting two pencils of radiation whose wavelengths are slightly different substantially simultaneously or simultaneously by passing the beam through a nonlinear optical device such as a mineral crystal or organic nonlinear optical system, in brief pulses or of weak intensity but continuously. This permits the creation of level curves which can be analyzed by conventional series logic analyses, e.g. by a Taylor, LaGrange or binomial series approach.

When noncoherent light is used, optical fibers can also be used, but a different analytical approach may be necessary, for example, holographic interferometry utilizing reference grids associated respectively with the emitter source and the receiver and means for determining or fixing the distance between the optic means of the analysis head and a plane of reference associated with a part of the body to be analyzed.

A dynamic solution, for example can comprise providing the analysis head of an ultrasonic or infrared emitter-receiver whose apparatus is to determine the distance of the head from the plane of reference at each instance in which analysis is effected. A static approach can provide an analysis head with a member of known length adapted to rest on a point of the portion of the body to be analyzed to establish a fixed distance.

It is possible, in accordance with the invention, also to use an optical fiber system with a graded reflective index (index gradient) to simplify the optical system and even allow elimination of lenses directed toward or away from the object This can be done with either coherent or noncoherent light.

The mirror system and the optics associated therewith provide more or less wide optics which permit analysis of relatively expensive areas and can deal with faces oriented differently from one to another or even faces which are not able to be directly illuminated and-/or observed.

The receiver which is sensitive to the reflected beam and possibly also to the reference beam, as described above, is advantageously a photosensitive element of the charge transfer type, preferably a CCD photosensitive matrix or even a modified vidicon tube. The advantages of a photosensitive matrix and a vidicon tube is that it allows analysis plane by plane and thus provides a three dimensional imaging. In practice, the number of gray levels is low and the analysis is able to determine positions in two dimensional space at intervals of say 20 microns without being adversely affected by the ability to generate the third dimension.

According to a feature of the invention, information storage means is provided between the receiver and the analog-numerical converter and supplies the signal processing means with a point by point output transformed by an interface into the numerical data necessary to control the machines. Means is provided to permit viewing of the data and possibly the image and is connected to the storage means.

This visualization of the image serves primarily for information and verification purposes and can allow viewing of the optical image as a whole at the conclusion of any tooth preparation work or even during the preparation operation and provides assurance that the preparation is being effected correctly.

It has been found to be advantageous to provide means permitting direct viewing of the image which is connected to the circuitry before the information undergoes analog-numerical conversion although the image can be generated line by line from the numerical data. In fact the visualization of the image allows the best image to be selected for generation of the numerical output and thus the apparatus can be of the interactive type permitting the operator to intervene in the process. Otherwise the system can operate entirely automatically.

The numerical processing prior to generation of a prosthesis, described in the case of a dental crown, will thus have a shape determined by the stump of the tooth as detected by the optical analysis described.

However, since generation of the outer shape of the prosthesis is also important, the analysis and signal processing means should also include:

means for determining and generating the shape of the envelope (outer shape of the dental prosthesis) or the volume which is to be included in the dental prosthesis;

means for determining and responding to the occlusion, static and dynamic, which may be expected once a prosthesis is introduced on the stump thereby allowing modification of the prosthesis to obtain a given bite condition or relationship to other teeth; and if possible, means for establishing and even possibly determining the color of the tooth to be fabricated, e.g. from analysis of the color, tint and pattern of adjacent teeth.

More particularly, the envelope or outer surface of the prosthesis can be considered as a volume defined by six planes which can be obtained by determination:

(a) from zones of contact or the boundaries defined by adjoining teeth, (b) by tangent planes to the arcade or determined on the basis of symmetry in the vestibular or lingual spaces, (c) by the lower boundary of the stump analyzed in the mouth for the lower plane, and (d) for the upper plane as a function of a mathematical analysis based upon the potential zone of contact between the maxillary set of teeth and the mandibular set of teeth upon closure.

When the method of the invention is applied to the automatic shaping of a removable prosthesis, the occlusion factors which enter into the determination of the shape, are deduced by the optical impression taken in the manner described but also from a facial and buccal analysis of the patient after a number of buccal adjustments, thereby avoiding the need for study of the temporal/maxillary articulation (ATM) by the extremely expensive classical means.

The occlusion can be determined by reference marking of the superior and inferior maxillaries taking separate optical impressions of the two maxillaries, forming an anterior optical grid of the adjustment markings of the two maxillaries and combining the two maxillaries based upon their reference marks at the level of the grid.

The automatic production of the prosthesis, for example, a crown, developed by the aforedescribed technique, can be carried out in a number of ways:

(1) The interior of the prosthesis can be shaped in accordance with the optically determined pattern of the stump with possible modification of the determined dimensions depending upon the manner in which the prosthesis is to be attached. Thus the circuitry can introduce a factor adjusting the space to receive a cement, or can minimize the space to permit a shrink fit or a gapless joint, with due consideration of the axis of insertion and any irregularities or the like left on the stump.

(2) The exterior shape can be developed in the manner described for determination of the envelope and stored in the memory, suitably adjusted for the desired occlusion.

(3) The nature of the prosthesis can be inputted, and determination made, e.g. by selection of color or tint.

A blank having the desired properties can thereupon be selected and fixed on the NC machine tool whose cutters or tools are appropriate to the dimensions and the curves of the prosthetic device to be fabricated. Vibration of the blank should be avoided on the workpiece carrier of the machine, thereby guaranteeing a fixed point of reference for the cutting operation as well.

Known methods of programming the NC machine tool in response to the numerical commands may be utilized and the prosthesis can be machined preferably under visual monitoring provided by the visualization means mentioned previously.

For a desired precision of about 50 microns, for example, we have found that about 5 minutes is required to machine a crown. The complete fabrication of a crown, including the optical image taking, requires about 15 minutes. This contrasts with the lost wax method which generally requires more than three hours of work by the dentist and the prosthetic technician and generally a period of the order of a week for travel.

The work time is thus reduced to a twelfth and the time from taking the impression to delivery of the prosthesis can be reduced by 1/600th. Throughout biological and physiologically required conditions are fulfilled and it is possible to provide a patient with a crown some 15 minutes after preparation of the stump has been completed in accordance with the present invention.

BRIEF DESCRIPTION OF THE DRAWING

The above and other objects, features and advantages of the present invention will become more readily apparent from the following description, reference being made to the accompanying drawing in which:

FIG. 1 is a highly schematic illustration of a first embodiment of the invention in which the radiant energy is coherent light and the source is a laser;

FIG. 2 shows a detail, in elevation, of an analyzing head illustrating principles of the invention;

FIG. 3 is a diagrammatic elevation, drawn to a scale which deviates from that of the actual structure, illustrating the apparatus of the invention;

FIG. 4 is a diagram showing part of the optical system for a noncoherent light source according to the invention;

FIGS. 5, 6 and 7 are somewhat diagrammatic elevational views illustrating other principles of the invention for use with a noncoherent light source;

FIGS. 8 and 9 are path diagrams showing optical imaging systems utilizing mirrors in the optical paths;

FIG. 16 is a plan view illustrating the determination of portions of the envelope from tangent planes for a crown;

FIG. 17 is another diagram illustrating the development of the exterior of the crown based upon the form and position of the stump analyzed by the optical imaging system of the invention;

FIG. 18 illustrates the definition of the planes and surfaces of the envelope for producing a mobile or removable prosthesis;

FIG. 19 is a diagram facilitating explanation of the positioning of the upper and lower images intervening in the determination of the actual occlusion;

FIG. 24 shows the simplified information flow for a movable prosthesis without antagonist;

FIG. 26 illustrates one approach to fabrication of the crown;

FIG. 27 illustrates another approach to crown fabrication utilizing a pin;

FIGS. 28, 29 and 30 illustrate various geometric fundamentals for the fabrication of a crown according to the invention;

SPECIFIC DESCRIPTION

Figure 9:
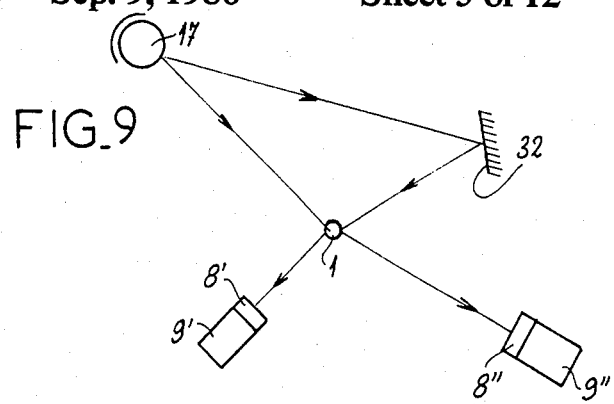

FIGS. 1–13 show various embodiments of the several aspects of the invention which permit three dimensional images, by interferometry, of the details of form and dimension of an object which has been described and illustrated as the stump of a tooth but adapted to receive a crown and ground to the frustoconical configuration shown to project above the gum area represented at 1a. It should be understood that these optical systems can be utilized to analyze shape and dimension of any other object in the odontological or medical field and, since the analysis generally is effected in the mouth, the probe, probes or analysis head must be dimensioned to fit comfortably in the mouth and to be handled by the practitioner.

In the embodiment of FIG. 1, a laser source 2 projects a beam of coherent radiation, light, through a filter 3 via a first optical fiber 4 and a lens 5 toward the zone of the stump 1 to be analyzed. The lens 5 at the outlet end 4a of the optical fiber or "light pipe" 4, serves to spread the incident beam 5a.

A condensing lens thus collects reflected light over the window 6a of reception, and delivers the reflected light to a second optical fiber 7 which delivers it to a receiver 8 in the form of an optical-electronic transducer whose electrical output is transformed into numerical signals by an analog-numerical or analog-digital converter 9.

The same transparent mirror 10 along the incident light path reflects a fraction of the light in a reference light beam through a condensing lens 12 of the receiver 8.

Utilizing the principles of this arrangement and as shown in FIG. 2 the analyzing head 13 can be provided at the end of a flexible cable containing the light pipes. In this embodiment, two objective lenses 6' and 6" collect the reflected rays from two opposite sides of the object 1 to be analyzed and are provided at the ends of respective optical fibers 7' and 7" which carry respective fractions of the reflected light, the respective receivers via the light pipes or optical fibers 7' and 7". The reference numeral 7, therefore, can refer to all of the optical fibers 7', 7" . . . carrying respective fractions of the reflected radiation to the associated receivers. In the embodiment of FIG. 2, two opposite faces are analyzed simultaneously and, by movement of the head around the tooth 3, dimensional analysis can be obtained. The head 13 is provided with a handle 14 from which the optical fibers 4 and 7 extend, and enabling manipulation of the flexible length of cable 14' between the head 13 and the housing 15 located externally of the mouth provided with emitter 2, the receiver 8 and the converter 9.

Each of the optical fibers 4, 7, 7', 7", etc. may be sheathed in an opaque flexible material to prevent damage to the eyesight of the operator or the patient.

FIG. 4 shows the principles of the present invention as applied to an apparatus which does not utilize coherent light.

Here the radiant energy sources 16 can each comprise a light generator 17, for example, a halogen lamp, a condensing lens or optical unit shown only diagramatically at 18, a reference grid 19 and an objective lens or lens system 20. A receiver 21 for the noncoherent light comprises a collecting objective 20a, as reference grid 19a and a receiver 8 which also is electrically connected to an analog-numerical converter in the manner described. The two reference grids or gratings 19 and 19a are of the micro-Moiré type having a threshold at $10^{-3}$ mm, close to the minimum.

The number of fringes or cross rulings can be determined with precision (from 1 mm to $10^{-3}$ mm with an ideal value at $10^{-2}$ mm). The distance separating the two optical centers should be known to about 0.5 mm and the focal point should be known to be about 1 mm. These various factors are fixed and defined by assembling the structure.

The Moiré pattern can create a reflection problem when the incident light is white light. To avoid this problem, it is possible to operate with a range of wavelengths which do not correspond to any color present in the mouth, for example by introducing a filter which passes blue or green light or light in the range between green and blue, in the incident light path. It remains to determine or fix the distance separating the plane of analysis of the receiver 8 from the reference plane lying, for example, below or at the lower border of the crown to be provided. This distance should be known to approximately 1 mm. According to the invention, we can fix this distance on an analysis head 13 by providing it with a probe 22 of a convenient length adapted to bear directly upon the tooth stump to be analyzed as shown in FIG. 5 which represents a particularly convenient construction corresponding to the principles of FIG. 4 and utilizing optical fibers 4, 7", 7" and lines 5, 6" and 6" as previously described. Since the position of the head is fixed, this fixes the distance between the reference plane R and the head and hence the distance between this reference plane and the receiver 8.

In FIG. 6 we have shown another mounting arrangement in which a single optical fiber provided with the lens 24 is formed with a pointer or probe 22, the lens and optical fiber here serving to supply the incident light beam and to retrieve the reflected light. The latter can be directed by a semitransparent mirror 25 to the receiver 8 associated with the converter 9.

The optical fibers may not always be necessary or desirable and hence, in FIG. 7, we show an analyzing head 113 in which a light source 17 and a receiver 8 are provided directly with the lenses 5 and 6 and are connected together to form this head. The head 113 is connected by electric cords 26 and 27 with an electric current source 28 and with the analog-numerical converter 9 provided in an external housing 29.

FIG. 8 shows a system which utilizes two mirrors 30 and 31 and which can be added to an optical system of the type previously described to generate the incident beam and to collect the reflected beam. The incident beam derives from a source 17 and the reflected rays are directed to the receiver 8. As is apparent from FIG. 9, which illustrates a variation of the system of FIG. 8, the incident beam can be trained upon object 1 from the source 17 directly and by a mirror 32 so as to envelope the object. Receivers 8' and 8" with respective analog-numerical converters 9' and 9" permit simultaneous analysis of two opposite faces of the object 1.

Figure 10:
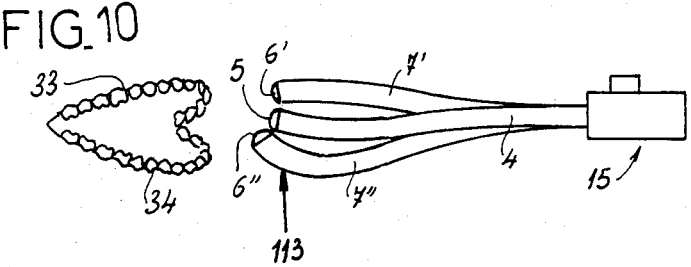
FIG. 10 is a diagram of the system as applied to the analysis of arcades of a patient.
Figure 11:
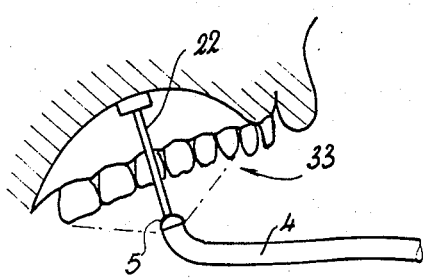
FIGS. 11, 12 and 13 are diagrams showing the imaging as applied to the mouth and tooth structures elsewhere than at the site of the prosthesis.
Figure 12:
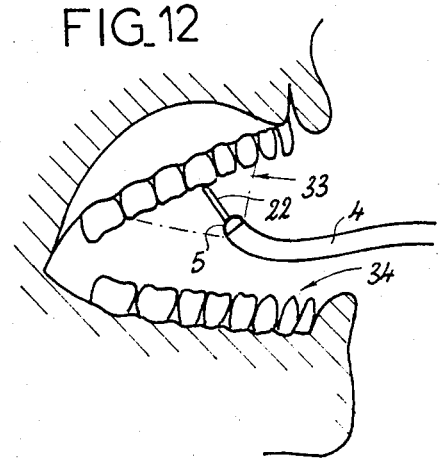
Figure 13:
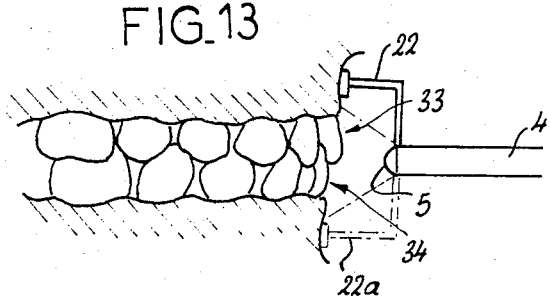

While the means previously described permits analysis of an object of relatively small dimensions, we have pointed out that it is advantageous as well to be able to analyze extended regions, e.g. to assist in developing the envelope or outer surface of the prosthesis to be fabricated. In FIG. 10, for example, we show the use of a head similar to the one already described for the analysis of the upper and lower arcades 33 and 34, or both, to establish the environment of the prosthesis in the buccal milieu. In principle this device is the same as the one described and comprises a housing containing the radiant source and the receivers, as well as the analog-numerical converters connected to these receivers. The housing 15 is connected by an optical fiber 4 to a lens 5 spreading the incident beam over the upper and lower arcades while other lenses 6' and 6" are fixed to the ends of the optical fibers 7' and 7" which pick up the reflected rays. The optics here can be considerably larger than those which must enter a limited region of the mouth and a pointer or probe such as that shown at 22 can here be used for positioning the head 113 with respect to any particular contact point in the mouth. In FIG. 11 we shall show that such a probe 22 abutting the upper palate while in FIG. 12, the probe is applied to one of the teeth. Of course, the input to the system may derive from a vestibular region (not shown) as well.

According to another feature of the invention, to the same end i.e. to enable effective siting of the prosthesis in its ultimate environment, we can effect an occlusion analysis of the frontal or lateral regions. With a probe abutting the vestibular surfaces as shown at 22 or 22a in FIG. 13. This also provides an analysis of the faces and is generally carried out after a number of facial reference marks have been applied. These reference marks can be provided preferably on the teeth, generally the incisors and premolars on the lower base of the maxillary and at the level of the condyle or the auditory foramen, thereby permitting a dynamic analysis with progressive movements of the jaw in occlusion and to the extremes of the mobility range.

In the medical and surgical realm, the numerical information can be obtained from a radiological analysis reconstituted in three dimensions or by coupling with a scanner or by vectoral correlation on a radiographic image or also by echography. Thus, we can utilize echography to assist in obtaining the optical image of a dental structure as a variant in the method previously described. The use of echographic waves is itself interesting, above all, in the determination of the contour of an organ.

Figure 14:
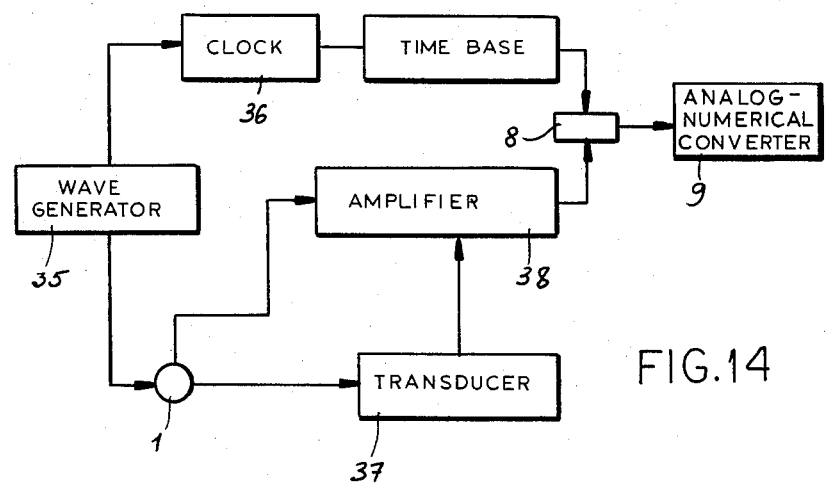
FIG. 14 is a block diagram illustrating the principles of the invention as applied echo determination of the shape of the stump and the use of a sonic or echograph technique.

As shown in FIG. 14 the echographic wave generator 35 can direct a sound wave front toward an object to be analyzed and controls a clock 36 generating a time base for the receiver 8 collecting the reflected signal via a transducer 37 and/or an amplifier 38, here as well the signals are delivered to a converter of the analog-digital type.

The process of the invention will be more readily understandable when the aspects thereof are considered with respect to the information flow diagrams of the drawing. Prior to discussing these information flow diagrams, it is important to note that, when the information is generated by a plurality of receivers, the images associated with the separate information sources must be merged or associated. This is done by the use of a reference point or elements, such as the stylus 22 or with respect to the circumference, whichever is more readily ascertainable.

It is only in this way that it is possible to establish that the entire shape has been analyzed. To this end, a space point analysis can be used, i.e. it is possible to verify whether the space between two points is constant since, if this is not the case, there is insufficient information for complete analysis of the particular region. Correction can be affected by connecting the most extreme points of a curve with the most proximal points and the total number of points will, of course, be a measure of the precision of the method.

We can also augment the values for any point as a function of the exigencies of the insertion of the prosthesis to take into consideration or compensate for erosion of section, physical properties of the cement used or the like. If a model having a "memory" is used, of course, such operations become useless.

Figure 15:
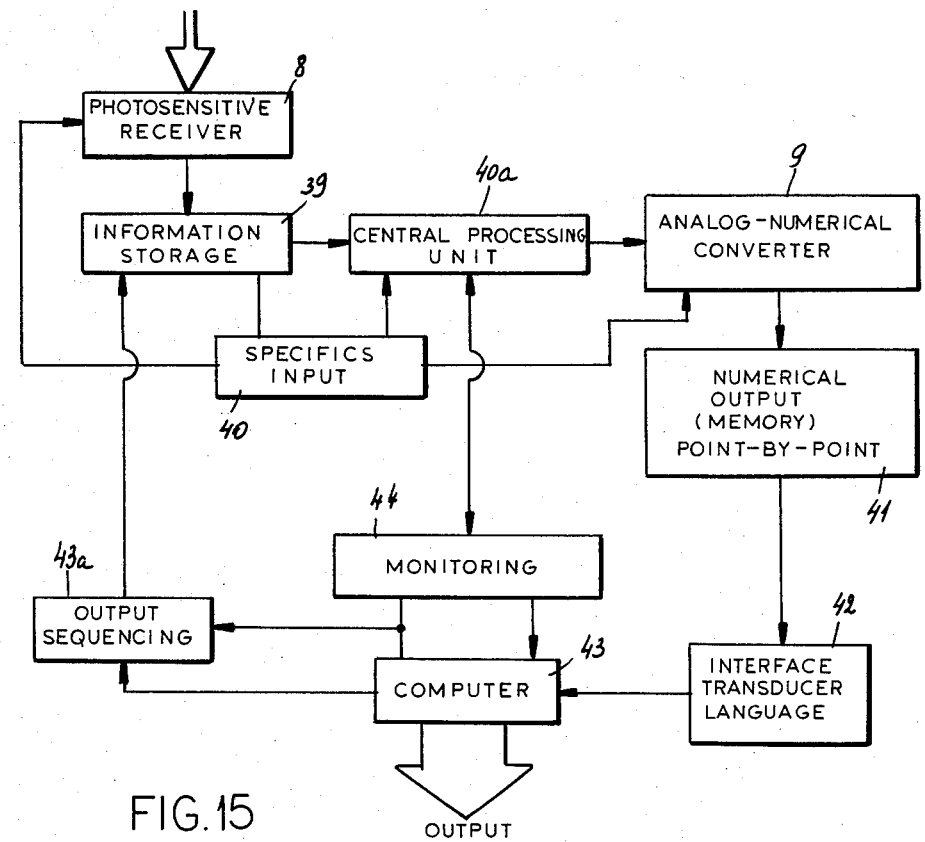
FIG. 15 is a block diagram showing the circuitry of the invention including the analog-numerical or analog-digital converter, the receiving means for the reflected radiant energy, and interactive means enabling visualization of the analyzed site and especially for use with a receiver of the CCD or charge coupled photosensitive mastrix type.

FIG. 15 represents the method aspects for receiving the reflected signal in greater detail. Using the algorithm represented in FIG. 15 we can carry out rapid and repetitive optical analyses with simultaneous viewing which permits choice of the best image and hence with intervention by the operator in an interactive system.

Photosensitive receiver 8, preferably a charge coupled photodiode matrix, supplies the information carried by the reflected rays to a memory or information storage 39 before this information is transformed by the analog-numerical converter 9 into the output. Control of the memory, the converter and the controller 40a is effected by a controller 40 which provides the specific feed excitation.

The converter 9 is connected to an output circuit 49 which, in turn, feeds an interface 42 whose output is applied to the calculator or computer 43. A video monitor 44 can serve as the visualizing means and preferably is a color video monitor and is interactively connected to the storage circuit 39. The output order is determined at 43a in part from inputs from the computer.

The analysis system utilizing the photosensitive CCD as shown generally in FIG. 15 requires a minimum of 100 gray levels with an antiblowing system to obtain sufficient information. The "x" and "y" coordinates are given automatically in plan view and are corrected ultimately as a function of the analysis and of the removal of the point under consideration from the vertical axis. The "z" coordinate is a result of a Fourier transformation whether the signal device from a coherent light source or a noncoherent light source, although a reference grid must be used in the latter case. The mathematical algorithms which can be employed here are conventional.

The means described thus far permit the generation of an optical image in three dimensions of a tooth stump 1 and a translation of the information representing this image into a numerical form which can be handled by conventional data processing equipment and which can be used for the operation of a numerically controlled machine. This information can be used to automatically machine a crown provided that other factors are introduced, e.g. the development of the envelope or outer surface of the crown.

Reference may now be had to FIG. 16 which deals with the determination of the envelope of the future crown 45 shown in dot-dash lines in this figure.

The envelope of the crown can be determined by a calculation of the interior volume thereof. This volume is defined by planes, including an anterior plane 46 and a posterior plane 47 theoretically tangent to the adjacent teeth 48 and 49 at the points of contact between these teeth and the tooth to be reconstituted and generated and whose practical determination can take into consideration corrective factors relating to physiological movement and to diastema.

This volume is also delimited by a lateral palatine or lingual plane 50 and by a lateral vestibular plane 51 which are tangent to the medial and lateral surfaces of the anterior and posterior teeth 48 and 49 respectively. At this point, as well, we can introduce factors relating to the type of tooth to be reconstituted, i.e. shape defining factors if, for example, the tooth is to resemble generally the shape of a lateral superior incisor, the tooth is to be substantially parallelopipedal, or is to have some other generally standard shape.

Data regarding such standard shapes can be stored in memory and recalled for the definition of the envelope, can be traced on the moniter utilizing a white pen or the like, and hence can be automatically or manually selected or defined. Finally the volume is defined by an upper or occlusal plane which can be determined with the mouth normally closed as the plane passing through a high point of the opposite tooth. Where the opposite tooth is missing, this plane is defined by the high points of the plane passing through the anterior and posterior adjacent teeth.

To determine the superior plane, we can utilize the following method of establishing the mandibular kinematics.

Firstly, an impression of the mandibular is taken with precision and thus the use facets of each tooth can be determined. These facets correspond to the sliding plane of the mandibular on the maxillary thereabove. These facets, therefore, represent impressions of the mandibular movements. It has long been known that in such studies one can scarcely reconstitute the movements with total precision.

To reference or mark these zones, it is sufficient to press the two maxillaries. The contact points lie forceably on these facets. If these planes of the respective teeth correspond, they are truly the planes of use of the mandibular. Knowing mathematically the relationship between the surface of use and the mandibular movements of these facets, the movements can be determined without requiring a dynamic study.

In the same manner, one can also determine the upper plane of the envelope. In applying to this plane the known rules with respect to occlusion, one can derive the plane by the zone of contact between the opposing tooth and the crown utilizing the tripodic, longcentric or other contact approach hitherto found to be convenient for stabilization of the arcade, for permitting mastication and for permitting normal displacements of the mandibular.

It is thus possible to obtain six planes which are tangent to the various external surfaces of a theoretical crown and, from these planes and the knowledge previously stored in memory, of the general shape of the tooth, the outer envelope can be established. The general shape can be a theoretical shape or it can be determined from an existing tooth using the head as previously described with appropriate correction for right-left symmetry. Of course, where the tooth was reasonably intact prior to grinding to form the stump, the general shape can be obtained by making an optical impression of the tooth before the grinding operation. In the latter case, the fabrication of the crown can be simplified because it is merely necessary to take an optical impression in the manner described before preparing the stump and then taking an optical impression of the stump and using the two optical impressions to generate the numerical control signals for the machine tool. When the prosthesis is to replace a number of teeth, the space to be occupied by the prosthesis is subdivided into a number of spaces, each of which has the envelope for the prosthetic teeth therein determined in the manner described.

In determining the external shape of the theoretical crown, it can be adapted, as illustrated in FIG. 17. In this case, the operation effectively brings in coincidence the lower surface A of the theoretical crown 45 at the lower plane of the envelope, with the contour B of the stump, ensuring a minimum thickness of the material e at the low point. This will guarantee that the stump will not be visible above the gum line, and conversely that the crown will not penetrate excessively deeply into the soft tissue. The theoretical external profile of the crown can be subjected to progressive correction while retaining the curvature and while ensuring that zones of contact with adjacent teeth 48 and 49 will be formed. For example, the correction may be a reduction in the outline from the outline shown at 45 and to the outline shown in solid lines. In this manner, the theoretical shape is progressively reduced until the minimum thickness e is reached while the other constraints described are maintained.

With respect to the upper portion of the tooth, a first correction can simply center the grooves of the theoretical envelope along the general line of the grooves of the teeth of the arcade. A second correction is then effected for the static occlusion state and corresponds to adaption of the occlusal surface of the theoretical tooth of the occlusal tooth of the opposite tooth shown in dot-dash lines at 52 in FIG. 17, so that, for example, the protuberances of the opposite tooth are juxtajposed with recesses of the theoretical but corrected envelope configuration and recesses of the opposite tooth are juxtajposed woth protuberances of the corrected profile.

A third correction is generated mathematically based upon the dynamic occlusion of the movements previously determined of the mandibular relative to the maxillary and can correspond to the movements of the arcade in general during the normal jaw movements. The envelope can also be determined by applying a deformable cap to the stump 1, having the patient engage in normal occlusion and thereby shape the upper plane, and analyzing the upper plane of the shaped cap in three dimensions utilizing the optical impression head of the present invention.

In the case of a removable prosthesis as shown in FIG. 18, the definition of the envelope is partially different. In this case, one must distinguish between an inferior plane 53, a superior plane 54 and a posterior plane 55, but the lateral and interior planes are joined by a single curved surface or envelope 56 which will be substantially tangent to the gingeval crest, but spaced therefrom by several millimeters. This space will be a function of the most vestibular part of the prosthesis (i.e. the free border of the incisors or the edge of the synthetic resin).

The lower limit of the surface 56 is fixed at a depth which is nontraumatic to the patient and is a function of the optical impression defining the lower plane 53. At the moment that this impression is taken, it is advantageous to have the patient flex the buccal muscles to be certain that their interaction with the surface 56 will be nontraumatic. The posterior plane 55 is determined by the anatomical elements located at the theoretical limits of the prosthesis, such as the retromolar tuberosity, the trigone, etc.

The upper plane 54, i.e. the occlusal plane of the prosthesis, can be determined by the actual position of the occlusal surface of the opposing set of teeth as described in connection with FIG. 19 herein below.

In the case where the prosthesis is to be juxtaposed with a set of teeth or at least a number of teeth remain as opposite teeth, an optical impression can be taken of the upper and lower arcades 33 and 34 as has already been described above, so that the anterior optical impression and the lateral optical impression define the anterior and lateral "screens" 57 and 58, respectively. The optical impressions of the upper and lower are then adjusted with respect to one another with the screens permitting mathematically exact positioning of them to obtain a condition of static occlusion corresponding to the occlusion of the maxillary and the mandible.

If there is or are no opposing tooth or teeth, one can operate in the manner described except that one can select the point of occlusion and thus define an intermaxillary ratio which is convenient.

For determining the dynamic occlusion, the movements of the jaw can be recorded, utilizing a similar mode of operation and/or by facial analysis of the patient utilizing the optical impression taking unit after a number of buccal reference marks are applied. If x-ray facial analysis is utilized, we can operate with three radio-opaque reference marks applied to the maxillary and visible to the optical impression-taking unit.

It is also possible to use emissive markers and to then employ an analysis table in which the emissive wave length is set forth. In this case too the markers should be visible to the optical impression-taking unit.

If a conventional reference marker is applied, it should be visible all during the analysis of the movements and the mark should be applied at locations and in such manner that their positions are fixed to a precision of 100 microns from starting to concluding the facial analysis.

If only intrabuccal marks are used, it is sufficient that they be visible all during the analysis of the movements.

Figure 20:
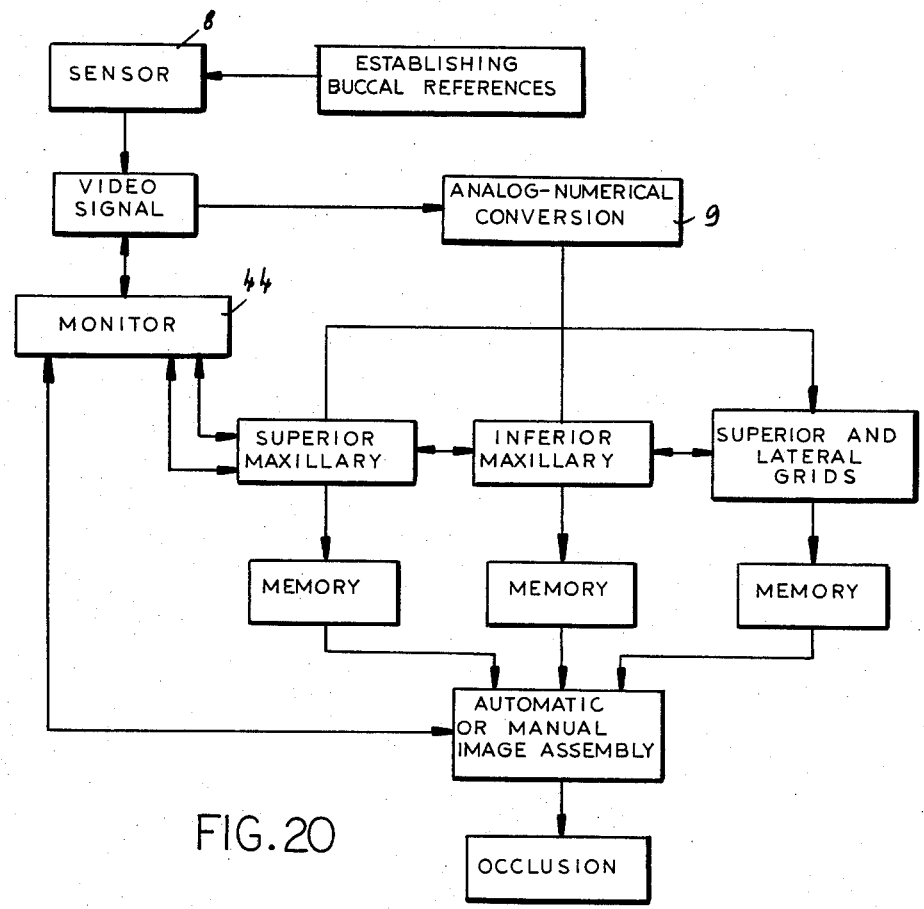
FIG. 20 is an information flow diagram significant to this explanation.
Figure 21:
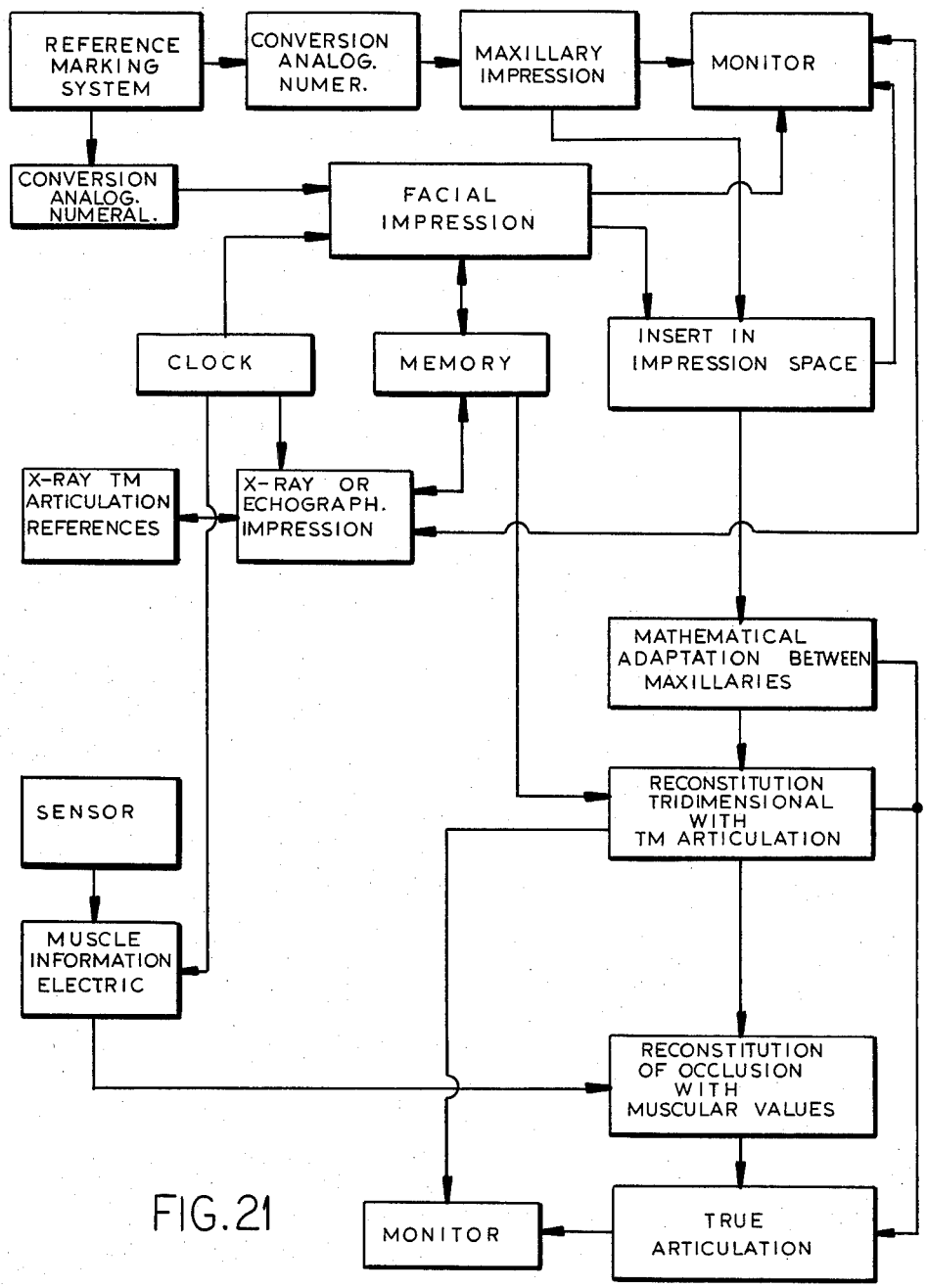
FIG. 21 is another information flow diagram showing the use reference markings and other receivers for taking into consideration pathology or characteristics of the temporal-maxillary joint.

The information flow diagram of FIG. 20 illustrates this latter operation as effected under the control of a viewing device or monitor 44. In the case of healthy patients, this analysis avoids the need for direct study of the temporal-maxillary articulation.

In the case of pathology, the method described may be combined with judicious analysis of muscular studies (tension, etc.) and with studying of this articulation and like factors. In the latter case, the internal reference marks and the external reference marks can include an endobuccal system which can be fixed on the teeth or on the gum, adhesively or by suction cups, and after recording the facial movements at external points, two optical impressions are taken, one with the reference points and the other for the prosthesis itself. It is thus sufficient to mathematically position the impression with respect to one another and thus not need to retain the markers. The facial movements permit determination of the mandibular movements in the space. Study of the temporal maxillary articulation permits evaluation of pathological cases with respect to occlusion and to improve the occlusion. This is also the case with muscular studies.

Figure 22:
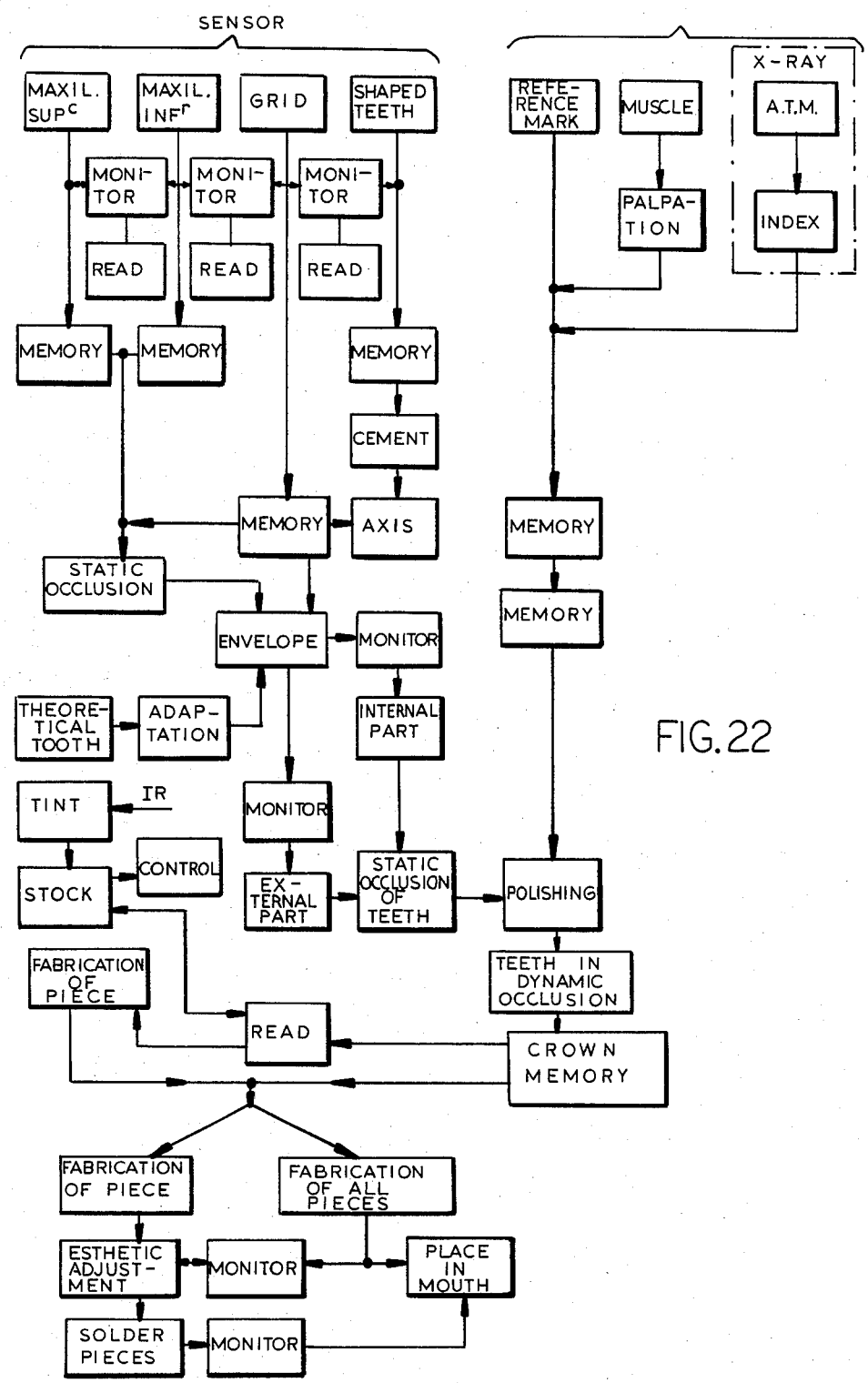
FIG. 22 is an information flow diagram appropriate to the definition of the characteristics of a fixed dental prosthesis and its fabrication utilizing the imaging method and apparatus of the invention.

In a variation, it is also possible to apply here the method of use facets explained previously and to thus determine mathematically all the movements of the mandibular without having studied them in a dynamic manner. With respect to a determination of the color, the tint or like characteristics of the crown, a tooth can be studied by a known thermographic process, preferably utilizing an infrared receiver of large aperture and subjecting it to illumination by infrared rays. The colors determined automatically are addressed, after visualization in full color, if desired to the memory which can be tapped for selection of the color of the crown to be fabricated. This method can be used to permit automatic production of esthetic surfaces by automatic inclusions of coloring agents or the like in successive layers of resin or ceramic which are utilized to automatically fabricate the tooth. The algorithm of FIG. 22 summarizes the operations necessary to define the esthetic characteristics of a fixed prosthesis and to utilize them in the case of optical impressions and other inputs in the manner described. The actual fabrication of the fixed prosthesis, namely crowns, will be described below.

When dealing with the fabrication of a mobile or removable prosthesis, consideration should first be given to a movable prosthesis having antagonist or an opposing tooth. In this case, the information which can be utilized includes: optical impressions of the two maxillaries, the frontal and lateral screens, and the general movements of the maxillaries.

The following approach is used:

Optical impressions are taken of the two maxillaries and the screens. After these have been viewed and the best image selected, an analog-numerical conversion is produced for the best image data and the results are stored. It is necessary to flex the muscles so that the inferior limit of the curved envelope surface 56 will be precise.

Then a static determination of a dynamic determination of the occlusion is made to limit further the envelope volume.

From the memory, information relating to the theoretical tooth shape can be withdrawn or a manual trace applied by a light pen to the monitor can permit the ideal shape of the prosthesis to be generated for the type of maxillary and within the envelope determined.

Recall from memory of the theoretical characteristics of a tooth permits, for the given prosthesis, adoption of color or tint, adoption of the occlusion and adoption of the mandibular movements in the manner described. For esthetic reasons, fabrication is effected separately for teeth on the one hand and the plate on the other.

The method of attachment on the plate or of the teeth can then be selected and the attachment part fabricated. The attachment methods can be such as to provide stable and detachable attachment which are automatic or manual.

Figure 23:
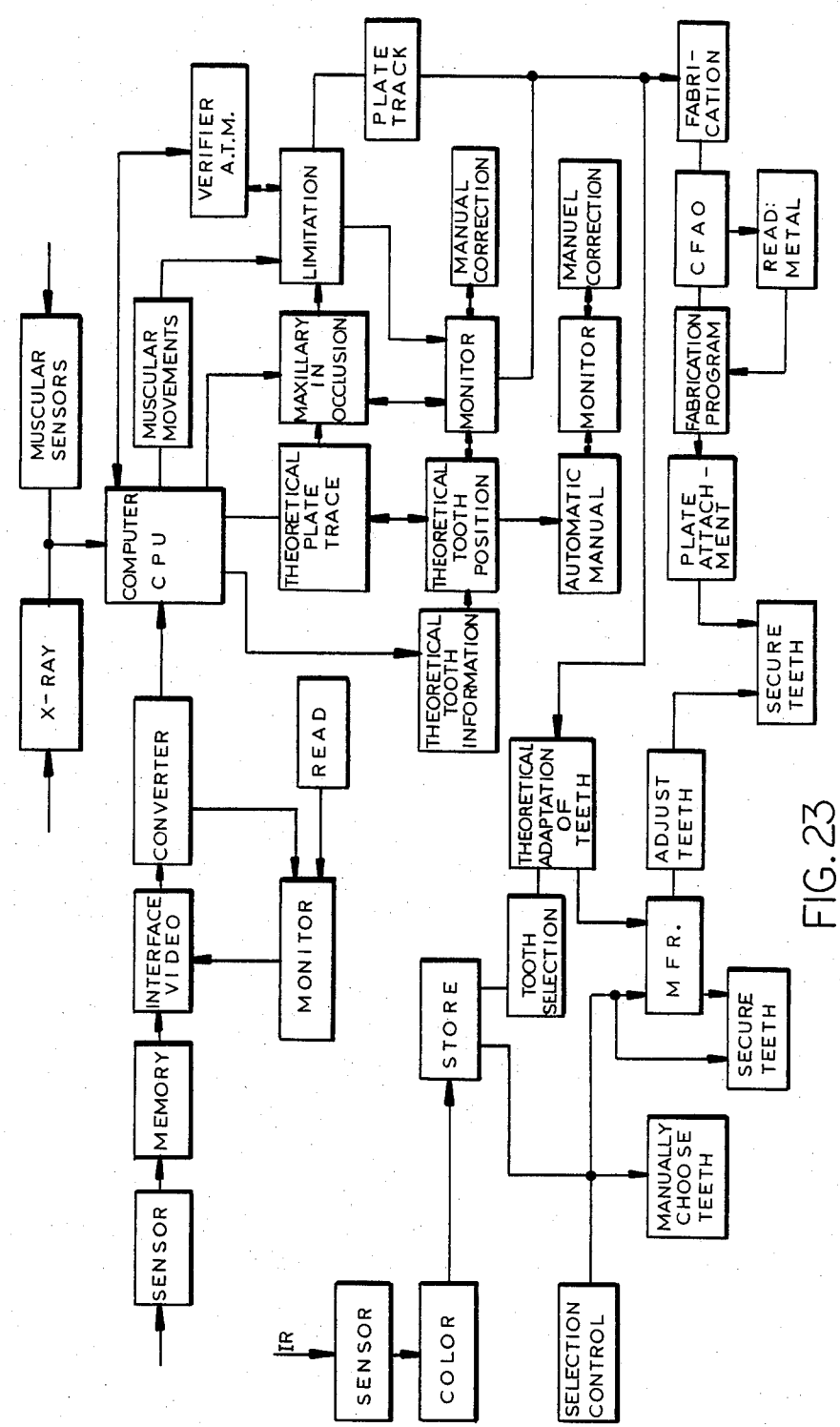
FIG. 23 is an information flow diagram as applied to a removable dental prosthesis in the case of a prosthesis with antagonist.

An echographic study is effected to determine the zones which are to be free from pressure (unloaded zones) which correspond to the gingeval regions. Each of these steps can be monitored and corrected using the visualization method described in the algorithm represented in FIG. 23. The adjusting operations during fabrication will be discussed further below.

For the fabrication of a mobile prosthesis without antagonist or opposing teeth, the operations are substantially identical but require a more exact evaluation of the rest positions of the musculature of the method and those at occlusion. For this reason, we provide a system substantially identical to that already described except for the complementary functions illustrated by the algorithm of FIG. 24 which permits a more precise analysis of the occlusion level:

Analysis of the rest position with the aid of muscle sensors and an analysis of the temporal-maxillary articulation.

Reduction of about 2 mm, for example, from the position obtained giving the occlusion position.

Theoretical combination of the two maxillaries at this latter position.

If there are teeth which can serve to support the prosthesis to be made, the computer will determine the ideal axis of insertion offering maximum stability and resulting from a combination of the dental axes considered separately where insertion is impossible, the adjustment can be made to the most stable teeth as chosen by the computer for determining the location of hooks or anchor points of the attachment under the best possible conditions.

In dentofacial orthopedics, the optical impression permits automatic study in vivo of the cast. This permits the development of a diagnosis and a treatment plan tooth by tooth in association with radiographic, echographic and thermographic techniques. By taking an optical impression of the arcade and of the maxillaries, it is possible to automatically calculate the constants which can be diagnostically evaluated.

In taking an optical impression of the face automatically, one can determine the basic facial constants. From the optical buccal impression and the optical facial impression, and by combining these with muscular and radiographic analysis, both the diagnostic processes and the selection of treatment can be automated in a manner which has not been possible heretofore.

By evaluating optical impression of the maxillaries and the radiological impressions of the teeth taken separately, the hooks applying traction to the teeth, their points of attachment on the teeth and/or their points of attachment to a movable prosthesis can be established in orthodonture, the same techniques can be used with, for example, an optical impression each year of a child for diagnosis automatically annually as to whether intervention is required or as to the nature of the intervention to be effected. Based upon the previews of the results empirically, it is possible to control each step of the treatment.

In dentistry, it is of course known to utilize photographs (as is the case in U.S. Pat. No. 3,861,044, previously mentioned) and it is important to recognize that a key difference with the device of the present invention is that it permits the obtaining of an optical impression which forms an image in three dimensions without use of of an intermediate support such as a photograph or other means for fixing the image. It also allows for direct storage of the information utilizing only an analog-numerical conversion which greatly simplifies information storage by comparison with the preceding systems.

When it is desired to determine the most advantageous volume of an insert or inlay adapted to plug a cavity, we can utilize the following sequence of steps, far more rapidly than heretofore:

1st step: Determination of the volume of the cavity.

2nd step: Determination of the envelop planes of the cavity.

3rd step: Determination of the static and dynamic occlusion.

4th step: Fabrication of the insert or inlay.

This mode of operation is thus identical to that which applies to the fabrication of fixed prostheses. In short, the volume of the pulp chamber is evaluated in the same way as the shape of a crown, with appropriate calibration of the instrument.

In paradontology, the exploratory device of the invention can resolve diagnostic problems in dealing with the temporal-maxillary articulation, the musculature and the dentition of the patient, as well as problems with respect to the relationship between the teeth and their bone support structures. In the first case, after applying reference marks for the occlusal articulation, the position of the condyle in the glenoid cavity and the state of muscular tension can be associated therewith. It is then possible to determine whether any dissymmetry is of an articular or muscular source and to establish whether there is any other pathology connected with this relationship. For dental diagnostics, the boney contour can be determined by echography or roentgenography, with respect to the dental and mucous contours, while the mobility of the teeth is determined by successive optical impressions in accordance with the techniques described.

In surgery, the system of the invention can be utilized to determine with great precision the position of an impacted tooth, especially using echography.

In implantology, if the cavity is open, the optical impression is taken locally in the manner described. However, if the cavity cannot be readily accessed, we may make use of echography or radiography from different angles. This permits use of implants adapted with high precision to the cavity to be filled and eliminates the need for prefabricated implants. For paraosseous implants, as may be used in major surgery, echographic visualization x-ray or penetrating wave visualization can be used to reference the contours of the bone exactly and to prepare displaying the piece on the monitor. In this way, we can provide a piece which can secure elements which may be fractured with great precision and guide the movements of the surgeon. It also permits developing the implants before the traumatized region is exposed or the surgical intervention is commenced.

The programming and interfacing with the operator will of course depend upon the nature of the information processed, i.e. the numerical data form, and permit visualization, control and safeguarding of the information. Control is effected from a console with an alphanumeric keyboard and provided with function command keys, a viewing screen or monitor and interactive graphic means which can be of any conventional type, permitting manipulation of the image, such as translation, change of scale and rotation. The information is processed rapidly in real time, always enabling storage of the operations which have been effected to shape a record of the patient and to permit other dental office or medical manipulations to be effected at a specific time. The images to be processed and the methods of fabrication depend essentially on the surfaces and volumes involved. The complex surfaces are defined by fractional interpolation from a network of points and curves upon which the tangency and curvature constants previously described are imposed.

Complex volumes are obtained by successive approximations of polyhedric volumes imposed by the limits of the optical envelope and by the insertion possibilities for the prosthetic piece. The final function, of course, is the actual fabrication of the prosthesis using a numerically controlled machine tool utilizing the information elements stored in the memory. The operator need not intervene at this point because most of these functions can be preprogrammed.

Figure 25:
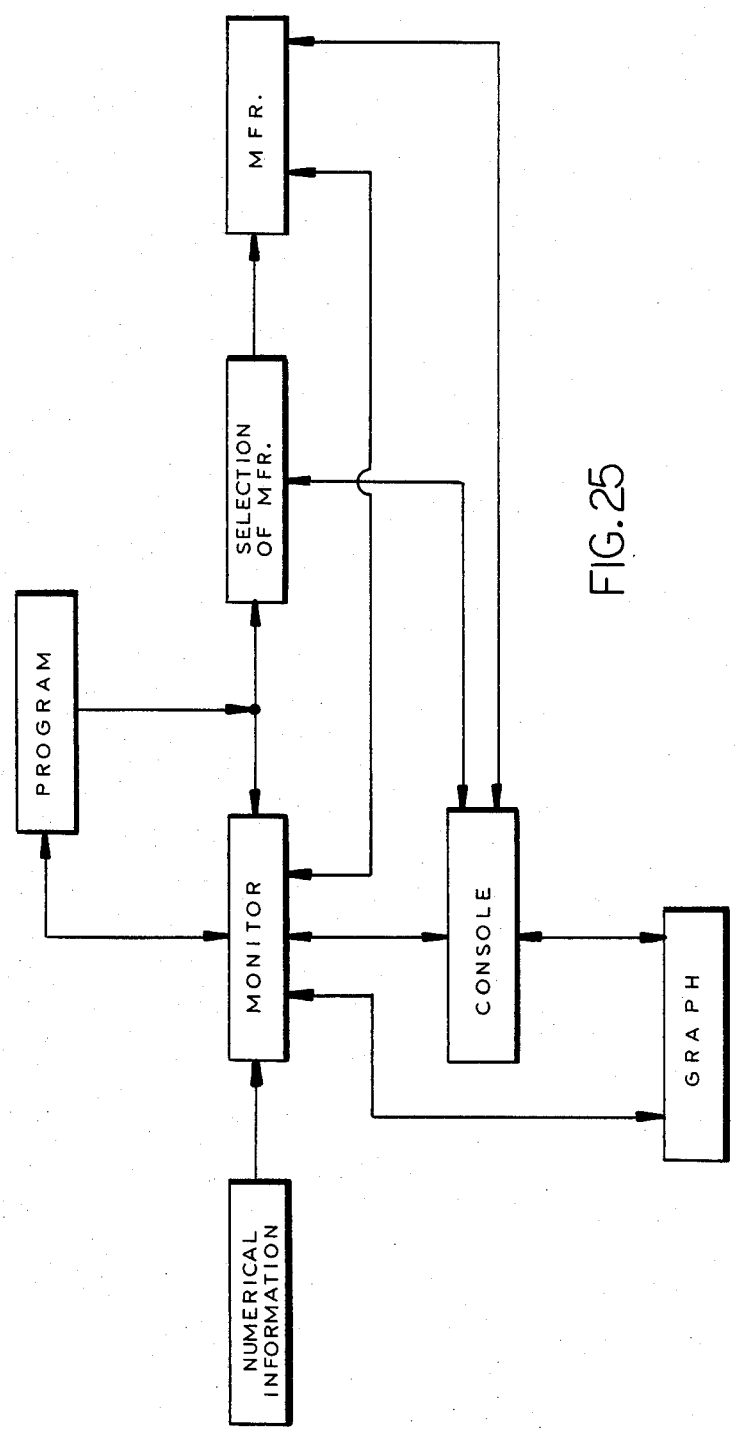
FIG. 25 is a block diagram illustrating the automatic machining of a prosthesis and control of the machine tool by the system of the invention.

The block diagram of FIG. 25 represents the principles of automatic fabrication of a prosthesis and control of the fabrication.

More particularly, we envisage two types of fabrication in the field of dental prosthesis and implantation, namely the manufacture of the support and the manufacture of one or more esthetic pieces to be affixed by the support in the oral cavity.

The production of the support is adapted to existing surfaces, e.g. those of a stump, determined by the techniques previously described. The part in contact with the mouth is thus fabricated according to known rules. For the upper part, however, various possibilities exist which are deserving of separate discussion.

For example, as shown in FIG. 26, a body 45 adapted to form the entire exposed surface of the crown and is internally provided with a cavity complementary in shape to the stump 1 and formed in one piece in the manner described. Here the body must, of course, consist of an esthetically satisfactory and biologically acceptable material, capable of being bonded to the stump and at the same time capable of being subjected to the rigors to which a dental crown may be subjected.

As shown in the lower portion of FIG. 26, the upper member 61 need not be internally shaped to correspond to the stump itself but may be formed of a standard shape, e.g. complementary to the outer configuration of a support 59 which, in turn, is internally machined in accordance with the principles of this invention based upon the optical impression of the stump while its external configuration may be shaped in accordance with a predetermined standard, the numerical data of which has been previously stored and is merely selected. In this case, protuberances 60 may be formed on the support and can engage in complementary recesses of the outer member 61 as shown for the crown 45' in FIG. 26.

When, however, the less developed stump must be utilized, e.g. because of damage to the tooth, the support 59'' can have a spike 62 which can be bonded in a tapered hole 1'' formed in the stump and detected in the taking of the optical impression, based upon which the support 59'' is formed. The support 59'' can be provided with an upwardly extending spike 60'' which penetrates into the outer member 61'' in forming the crown 45'' of FIG. 27. The spike or pin 62 can be threaded.

The projections 60, 60'' can, of course, be fixedly positioned and shaped with considerable accuracy, since they do not depend on optical impressions or the like, and can be attached to the upper members by any conventional means such as cement, metal, snap fasteners or other attachments, including screw threads and dental adhesives.

In surgery and in dentofacial orthopedics, we may fabricate supports which can serve as anchors for springs, or we may provide plates or the like for temporary retention in the mouth for orthodontic esthetic considerations.

The various pieces to be fabricated, are, of course, shaped based upon the geometry and dimensions determined by the stored data. It is possible to start from simple geometrical tooth shapes as determined by their projections in two different planes, thereby eliminating a point by point construction of the shape which is desired in space and saving time and work in the numerical control machine.

From the standard shapes, the three dimensional correction can be made and, if desired, the machine can also select the nature of the material and the color and tint by numerical selection. Where the machine has a plurality of tools, the tools and the succession in which they are used are numerically selected, and, of course, the numerical control commands will select the advance or retraction of the workpiece and the tool and the relative movements thereof.

The numerical control machine can be a milling machine, an electroerosion machine using EDM (electric discharge machining) supplied with a succession of closely spaced machining pulses and a fine electrode, an electrochemical machining tool, e.g. of the cavity-sinking type, an electroforming machine for deposition of material, a chemical shaping system utilizing masks and the like for selectively removing material or depositing material, ultrasonic shaping machines and high energy shaping machines using lasers or the like, or combinations thereof with numerical control of transfer of the workpiece between such machines or between stations at which the operations normally effected in such machines are carried out. Finishing can be effected also automatically and can include the steps of cleaning, soldering, polishing, etc.

The machining operation can comprise removing material from a workpiece in order to impart the calculated ideal form to the latter. For this purpose, it is sufficient to utilize conventional numerical control technology to generate a numerical command program permitting the shaping of the interior and exterior of the prosthesis, to use tools which can achieve this result and to orient the workpiece and the tools and the respective trajectories to obtain the desired shape. Micromilling can be used, for example, to shape a crown and in accordance with the numerical control program, we may divide the shaping operation into three principal stages.

Firstly, we can shape the base of the crown as a closed contour 63 (FIGS. 28-30) constituted by straight line segments D or semicircles C to which the straight line segments are tangent. The radius of the smallest circle C will always be greater than that of the tool at the point of contact.

The flank of the crown extends from the contour 63 and has a divergence alpha or beta (FIG. 29) from the perpendicular to the plane of the base 63 of the crown along the boundary thereof.

Figure 31:
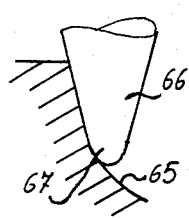
FIGS. 31-33 are diagrammatic elevational views illustrating the fabrication of the crown by machining a blank with tools of different shapes.
Figure 32:
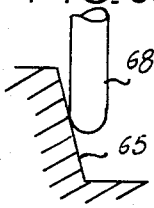
Figure 33:
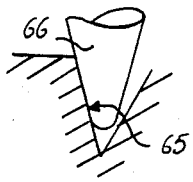

The base of the crown is machined exclusively as a function of assembling adjacent machining planes 64 so as to prevent the crown from having any gum engaging portion (see FIG. 30). This base is delimited along its perimeter by the flank 65 of the crown. The junction between the base and the flank has a radius which is a function of the spherical end of the tool and is the stump for all reentrant dehedrals. The choice of the tool will depend upon the shape and dimension of the crown to be made. For machining the flank 65, for example, we may use a conical tool 66 (FIG. 31) whose half angle at its apex is equal to the angle of the skin surface. The end of a generally cylindrical tool 68 may be utilized to produce the flank 65 in a number of passes (FIG. 32) while the plane 64 of the base defines the lower limit of the tool 66 or 68 (FIGS. 31-33).

Figure 34:
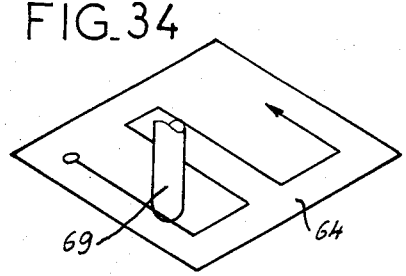
FIG. 34 is a diagrammatic perspective view illustrating the machining of the base of a crown.
Figure 35:
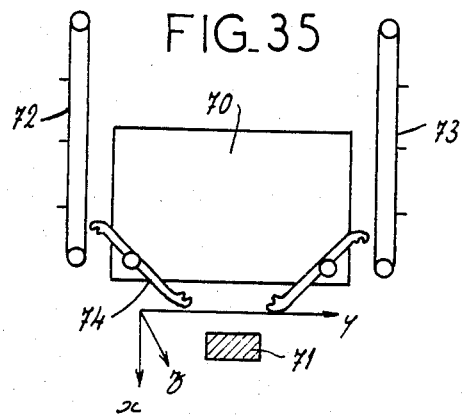
FIG. 35 is a diagrammatic view of a numerically controlled machine for use with the present invention.

To machine the base of the crown, a tool 69 having a spherical bottom end can be used, the radius of which is equal to the radius to be formed at the bottom. Machining of the bottom is effected level by level with linear and parallel passes delimited by adjacent planes and/or by the flanks of the crown. In a general program for this purpose, it is necessary to admit of a number of base contours for the number of bottom planes and thus their relative disposition (see FIG. 34). A diagram of the principles of machining utilizing numerical control has been shown in FIG. 35 in which the numerical controller is represented at 70. The zone which is to be machined in accordance with movement in three coordinates x, y and z has been represented at 71.

The machine is located between magazines 32 and 33 which feed the material to be machined, namely a selected workpiece having the properties desired and a tool from a collection of tools. The machine 70 comprises an arm 74 for transferring the workpiece to the workpiece holder and an arm 75 for changing the tool, the magazines moving past these arms until they are halted by the numerical control.

Figure 36:
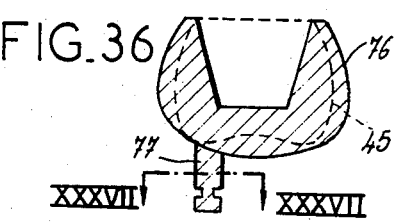
FIG. 36 is a vertical section through a blank for forming a crown and having a tenon at which the workpiece can be affixed to the machine tool.
Figure 37:
FIG. 37 is a section taken along the line XXXVII—XXXVII of FIG. 37.

The assembly of crown blanks 76 (see FIG. 36) is selected by the computer as a function of volume or other characteristics for the crown to be fabricated as formed. The outline of the crown 45 to be shaped has been shown in broken lines in FIG. 36. Each blank 76 is provided with an attachment projection 77 which will ultimately be removed but which serves to enable the blank to be secured on the machine. Preferably the projection 77 is of rectangular cross section as shown in FIG. 37.

The removed material, in the form of chips, filings or the like can be recycled to a foundry or other location at which the blanks are prepared for reuse.

Naturally, the invention is not limited to embodiments described to show the best mode of the invention, but embraces modifications within the spirit and scope of the appended claims.

For example, the receiver 8 may be utilized at a different point in time for vectoral correlation between two radiographic images or photographic images taken at different angles to thereby provide some or all of the information required for the optical impressions.

The analog-numerical converter 9 will preferably be in the form of a microprocessor which can be incorporated in the endobuccal assembly in a device similar to that shown in FIG. 7.

It is possible to use a first optical fiber of circular cross section to guide the instant beam and a second optical fiber of annular cross section, serving the first to guide the reflected beam.

In the optical system, it is possible to use not only mirrors, but also prisms in association with the fiber optics to permit lateral observation of the parts of the mouth which are accessible only with difficulty.

We claim:

1. A system for taking an impression of a body region for the production of a prosthesis comprising:
   at least one source of nontraumatic light wave energy for generating waves and directing same at a body region to be examined whereby said waves are reflected from said region;
   at least one receiver for said waves reflected from said region for generating analog intensity values representing waves reflected from said region;
   an analog-numerical converter connected to said receiver for transforming said analog intensity values representing the waves reflected from said region into numerical information representing characteristics of said region;

means receiving said numerical information for three-dimensional analysis of the shape and dimensions of said region from said numerical information and for designing a three-dimensional shape corresponding to a finished prosthesis with a contour adapted to fit said region; and signal processing means connected to said means receiving said numerical information for transforming an output thereof into machine command signals for direct automatic control of a machine for the direct production of a prosthesis by machining of a workpiece to fit precisely to said region, said source being a source of coherent light, at least one optical fiber connected to said source of coherent light, and at least one lens associated with the optical fiber for directing coherent light onto said region, said receiver comprising a collecting lens, another optical fiber associated with said collecting lens, and a transducer connected to said other optical fiber for receiving reflected coherent light from said region, said system further comprising a reference optical path for bypassing a portion of light from said source directly to said receiver to serve as a reference enabling interference analysis of said region.

2. A system for taking an impression of a body region for the production of a prosthesis comprising:

at least one source of nontraumatic light wave energy for generating waves and directing same at a body region to be examined whereby said waves are reflected from said region;

at least one receiver for said waves reflected from said region for generating analog intensity values representing waves reflected from said region;

an analog-numerical converter connected to said receiver for transforming said analog intensity values representing the waves reflected from said region into numerical information representing characteristics of said region;

means receiving said numerical information for three-dimensional analysis of the shape and dimensions of said region from said numerical information and for designing a three-dimensional shape corresponding to a finished prosthesis with a contour adapted to fit said region; and signal processing means connected to said means receiving said numerical information for transforming an output thereof into machine command signals for direct automatic control of a machine for the direct production of a prosthesis by machining of a workpiece to fit precisely to said region, said waves being noncoherent light waves, and the region being analyzed by interferometric holography, said system comprising respective reference grids associated with said source and with said receiver, and means for establishing a predetermined distance between the source and the receiver and a plane of reference at said region.

3. The system defined in claim 2, further comprising a filter associated with said source for filtering from a noncoherent light directed at said region, light of a wavelength corresponding to colors present at said region and permitting the passage only of light having a wavelength between blue and green wavelengths inclusively.

4. The system defined in claim 2 wherein said source and said receiver include portions forming an analysis head adapted to be inserted into the mouth of a patient to examine a dental region thereof constituting said region to be analyzed, said head being provided with at least one transmitter of energy and at least one receiver for corresponding energy for establishing the distance between said head and said reference plane.

5. The system defined in claim 2 wherein said source and said receiver include portions forming an analysis head adapted to be received in the mouth of a patient for examination of a dental region, said head being provided with a probe of fixed length adapted to rest against a point of said region for establishing a predetermined distance between said head and said reference plane.

* * * * *